United States Patent [19]

Baudoin et al.

[11] Patent Number: 5,750,567
[45] Date of Patent: May 12, 1998

[54] FARNESYL TRANSFERASE INHIBITORS, PREPARATION THEREOF AND PHARMACEUTICAL COMPOSITIONS CONTAINING SAME

[75] Inventors: Bernard Baudoin, Chaville, France; Christopher Burns, Rosemont, Pa.; Alain Commercon, Vitry-Sur-Seine; Alain Le Brun, Vigneux, both of France

[73] Assignee: Rhone-Poulenc Rorer SA., Antony Cedex, France

[21] Appl. No.: 875,005

[22] PCT Filed: Jan. 16, 1996

[86] PCT No.: PCT/FR96/00067

§ 371 Date: Jul. 15, 1997

§ 102(e) Date: Jul. 15, 1997

[87] PCT Pub. No.: WO96/22278

PCT Pub. Date: Jul. 25, 1996

[30] Foreign Application Priority Data

Jan. 18, 1995 [FR] France .................. 95 00494

[51] Int. Cl.⁶ .................................................. A61K 31/21
[52] U.S. Cl. .......................... 514/510; 514/560; 514/562; 560/10; 560/427
[58] Field of Search ........................ 560/10; 562/427; 514/510, 560, 502

[56] References Cited

U.S. PATENT DOCUMENTS 5,523,456  6/1996  Stokker et al. .
5,536,750  7/1996  DeSolms et al. .

FOREIGN PATENT DOCUMENTS 9409766  5/1994  WIPO .
9410138  5/1994  WIPO .

*Primary Examiner*—Samuel Barts
*Attorney, Agent, or Firm*—Raymond S. Parker, III; Michael B. Martin; Martin F. Savitzky

[57] ABSTRACT

Novel farnesyl transferase inhibitors of general formula (I)

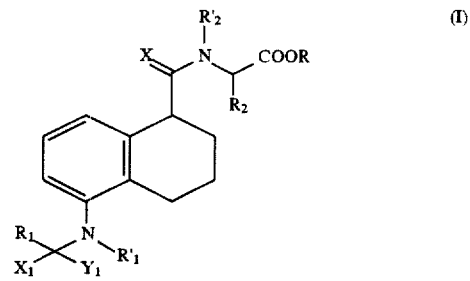

preparation thereof and pharmaceutical compositions containing same. In general formula (I), $R_1$ is $Y—S—A_1—$ (where Y is a hydrogen atom, an amino acid residue, a fatty acid residue, or an alkyl or alkoxycarbonyl radical, and $A_1$ is a $C_{1-4}$ alkylene radical optionally α-substituted in the $>C(X_1)(Y_1,)$ grouping by an amino, alkylamino, alkanoylamino or alkoxycarbonylamino radical wherein the alkyl or alkanoyl portion contains 1–6 carbon atoms; each of $X_1$ and $Y_1$ is a hydrogen atom or $X_1$ and $Y_1$, taken toether with the carbon atom to which they are attached, form a $>C=O$ grouping; $R'_1$ is hydrogen or a $C_{1-6}$ alkyl radical; X is an oxygen or sulphur atom; $R_2$ is a $C_{1-6}$ alkyl, alkenyl or alkynyl radical optionally substituted by hydroxy, alkoxy, mercapto, alkylthio, alkylsulphinyl or alkylsulphonyl.

5 Claims, No Drawings

FARNESYL TRANSFERASE INHIBITORS, PREPARATION THEREOF AND PHARMACEUTICAL COMPOSITIONS CONTAINING SAME

This application is a 371 of PCT/FR96/00067 filed Jan. 16, 1996.

The present invention relates to new farnesyl transferase inhibitors of general formula:

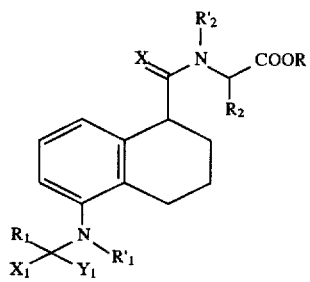

optionally to their salts, to their preparation and to the pharmaceutical compositions which contain them.

The inhibition of farnesyl transferase, and consequently of the farnesylation of the Ras protein, blocks the capacity of the mutated Ras protein to transform normal cells into cancerous cells.

The C-terminal sequence of the Ras gene contains the unit "CAAX" or "Cys-Aaa$_1$-Aaa$_2$-Xaa", in which Aaa represents an aliphatic amino acid and Xaa represents any amino acid.

It is known that tetrapeptides with a CAAX sequence can inhibit the farnesylation of the Ras protein. For example, peptide inhibitors of farnesyl transferase, Cys-Aaa$_1$-Aaa$_2$-Xaa, which are especially represented by the peptides Cys-Val-Leu-Ser, Cys-Val-Ile-Met and Cys-Val-Val-Met which manifest their inhibitory activity at concentrations in the region of $10^{-6}$M or of $10^{-7}$M, have been described in PCT Application WO 91/16340 and in Application EP 0,461,869.

It has now been found, and this forms the subject of the present invention, that the peptides of general formula (I) manifest their inhibitory activity (IC$_{50}$) at concentrations of the order of $10^{-8}$ or of $10^{-9}$M.

In the general formula (I), R$_1$ represents a radical of general formula Y—S—A$_1$— in which Y represents a hydrogen atom or an amino acid residue or a fatty acid residue or an alkyl or alkoxycarbonyl radical, and A$_1$ represents a straight or branched alkylene radical containing 1 to 4 carbon atoms, optionally substituted at the position a to the >C(X$_1$) (Y$_1$) group by an amino, alkylamino, alkanoylamino or alkoxycarbonylamino radical, the straight or branched alkyl or alkanoyl part of which contains 1 to 6 carbon atoms, X$_1$ and Y$_1$ each represent a hydrogen atom or form, together with the carbon atom to which they are bonded, a >C=O group, R'$_1$ represents a hydrogen atom or a straight or branched alkyl radical containing 1 to 6 carbon atoms, X represents an oxygen or sulphur atom, R$_2$ represents a straight or branched alkyl, alkenyl or alkynyl radical containing 1 to 6 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when R$_2$ represents an alkyl radical substituted by a hydroxyl radical, R$_2$ can form a lactone with the carboxyl radical at the α position, R'$_2$ represents a hydrogen atom or a straight or branched alkyl radical containing 1 to 6 carbon atoms, and R represents a hydrogen atom or an alkyl radical containing 1 to 6 carbon atoms, optionally substituted by an alkoxy radical containing 1 to 4 carbon atoms, an alkylthio radical containing 1 to 4 carbon atoms, an alkylsulphinyl radical containing 1 to 4 carbon atoms, an alkylsulphonyl radical containing 1 to 4 carbon atoms, a phenyl radical, a phenoxy radical, a phenylthio radical, a phenylsulphinyl radical, a phenylsulphonyl radical, an alkylamino radical containing 1 to 4 carbon atoms or a dialkylamino radical in which each alkyl part contains 1 to 4 carbon atoms, or a phenyl radical, optionally substituted by one or a number of atoms or radicals chosen from halogen atoms and alkyl, alkyloxy, alkylthio or alkanoyl radicals.

More particularly,

R$_1$ represents a radical of formula Y—S—A$_1$— in which Y represents a hydrogen atom or a lysine residue or a fatty acid residue containing up to 20 carbon atoms and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom or a methyl radical, X represents an oxygen atom, R$_2$ represents an alkyl radical containing 1 to 4 carbon atoms, optionally substituted by a hydroxyl, methoxy, mercapto, methylthio, methylsulphinyl or methylsulphonyl radical, R'$_2$ represents a hydrogen atom or a methyl radical, and R represents a hydrogen atom or an alkyl radical containing 1 to 4 carbon atoms, optionally substituted by an alkoxy radical, or a phenyl radical.

More particularly still,

R$_1$ represents a radical of formula Y—S—A$_1$— in which Y represents a hydrogen atom and A$_1$ represents an ethylene or propylene radical optionally substituted by an amino radical, X$_1$ and Y$_1$ each represent a hydrogen atom or form, together with the carbon atom to which they are bonded, a >C=O group, R'$_1$ represents a hydrogen atom, X represents an oxygen atom, R$_2$ represents a methyl, ethyl, propyl or butyl radical optionally substituted by a hydroxyl, methoxy, mercapto or methylthio radical, R'$_2$ represents a hydrogen atom, and R represents a hydrogen atom or an alkyl radical containing 1 to 4 carbon atoms.

The products of general formula (I) in which R$_1$ represents a 2-mercaptoethyl or 1-amino-2mercaptoethyl radical, X$_1$ and Y$_1$ each represent a hydrogen atom or form, together with the carbon atom to which they are bonded, a >C=O group, R'$_1$ represents a hydrogen atom, X represents an oxygen atom, R$_2$ represents an n-butyl or 2-(methylthio) ethyl radical and R'$_2$ represents a hydrogen atom, and R represents a hydrogen atom or a methyl radical are very particularly advantageous.

The present invention also relates to the stereoisomeric forms of the products of general formula (I). The amino acid residues represented by $R_1C(X_1)(Y_1)(NR'_1)$ and $R'_2CH(NR'_2)CO-OH$ preferably have the configuration of the natural amino acids.

The present invention also relates to the inorganic or organic salts of the products of general formula (I).

The new products according to the invention can be prepared by the application of known methods derived from the methods used more particularly in peptide chemistry for chain assembly.

Generally, the products of general formula (I), which $X_1$ and $Y_1$ form, together with the carbon atom to which they are bonded, a >C=O group and X represents an oxygen atom, are obtained from 5-nitro-1,2,3,4-tetrahydronaphthyl-1-carboxylic acid, with which is condensed an amino acid of general formula:

(II)

in which $R_2$ and $R'_2$ are defined as above and R' represents an alkyl radical containing 1 to 4 carbon atoms which is optionally substituted by a phenyl radical, preferably a tert-butyl radical, the reaction being carried out in the presence of a coupling agent, such as hydroxybenzotriazole and dicyclohexylcarbodiimide, and of a base, such as triethylamine, in an organic solvent, such as dimethylformamide, in order to give a product of general formula:

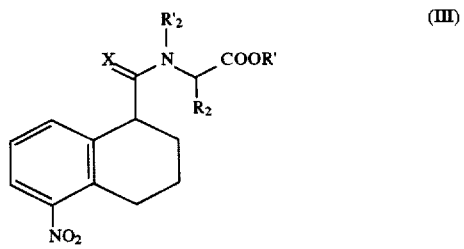

(III)

in which X represents an oxygen atom and $R_2$, $R'_2$ and R' are defined as above, which is reduced, preferably by means of stannous chloride, to a product of general formula:

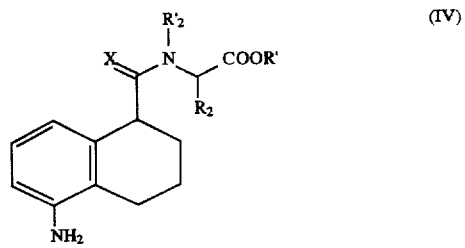

(IV)

in which X represents an oxygen atom and $R_2$, $R'_2$ and R' are defined as above, with which is condensed a product of formula:

(V)

in which $R_1$ is defined as above and $X_1$ and $Y_1$ form, together with the carbon atom to which they are bonded, a >C=O group, it being understood that the amino and mercapto functional groups carried by $R_1$ are optionally protected by appropriate protecting groups, such as a trityl radical for the mercapto functional group or a tert-butoxycarbonyl radical for the amino functional group, the reaction preferably being carried out in the presence of an alkyl haloformate (isobutyl chloroformate) and of an organic base (N-methylmorpholine) in an inert organic solvent (tetrahydrofuran), in order to obtain a product of general formula:

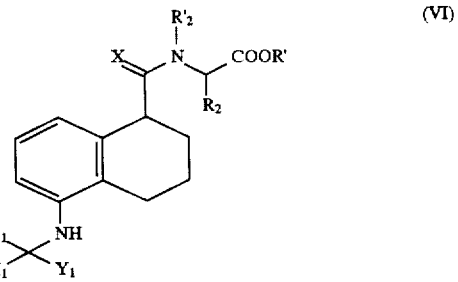

(VI)

in which the symbols X, $X_1$, $Y_1$, $R_1$, $R_2$, $R'_2$ and R' are defined as above, the protective groups of which are replaced by hydrogen atoms, by means of trifluoroacetic acid in the presence of ethanedithiol, when the protective groups represent trityl, tert-butoxycarbonyl or tert-butyl radicals, in order to obtain a product of general formula (I) in which $X_1$ and $Y_1$ form, together with the carbon atom to which they are bonded, a >C=O group.

Generally, the products of general formula (I) in which the symbols $X_1$ and $Y_1$ each represent a hydrogen atom can be obtained by reaction of an aldehyde of general formula:

$R_1-CHO$ (VII)

in which $R_1$ is defined as above, it being understood that the amino and mercapto functional groups carried by $R_1$ are optionally protected by appropriate protective groups, such as a trityl radical for the mercapto functional group or a tert-butoxycarbonyl radical for the amino functional group, with a product of general formula (V) in the presence of a reducing agent, such as, sodium cyanoborohydride, sodium borohydride, sodium triacetoxyborohydride or hydrogen in the presence of a catalyst. Generally, the reaction is carried out in an organic solvent such as an alcohol, for instance methanol, optionally in combination with another organic solvent such as an ether, for instance tetrahydrofuran. It is particularly advantageous to carry out the reaction in anhydrous medium.

Condensation of the aldehyde with the amine having been carried out, the protecting groups are replaced by hydrogen atoms by application of the usual techniques. Thus, the Boc or trityl or tert-butyl protecting groups can be replaced by hydrogen atoms by means of trifluoroacetic acid in the presence of ethanedithiol.

The products of general formula (I) in which X represents a sulphur atom can generally be obtained from a product of general formula (III) in which X represents an oxygen atom by thionation and then by carrying out the reduction, condensation or reductive amination, according to the situation, and deprotection stages described above for the preparation of a product of general formula (I) in which X represents an oxygen atom.

When, in the general formula (I), the $R_2$ symbol forms a lactone with the carboxyl functional group in the a position, treatment in basic medium of the corresponding product leads to the product of general formula (I) in which $R_2$ represents an alkyl radical substituted by a hydroxyl radical. Generally, opening of the lactone takes place as soon as the pH becomes greater than 7. It is particularly advantageous to carry out the reaction in the presence of an inorganic base (sodium hydroxide or potassium hydroxide) in aqueous/alcoholic medium, such as a water/methanol mixture.

The products of general formula (I) in which R represents an optionally substituted alkyl radical or an optionally substituted phenyl radical as indicated above can be obtained by esterification of a product of general formula (I) in which R represents a hydrogen atom under the usual esterification conditions which do not affect the remainder of the molecule.

The products of general formula (I) in which R represents a hydrogen atom can also be obtained by saponification of a product of general formula (VI), followed by replacement of the protective groups carried by $R_1$ under the conditions described above.

5-Nitro-1,2,3,4-tetrahydronaphthyl-1-carboxylic acid, which can be obtained as a mixture with 7-nitro-1,2,3,4-tetrahydronaphthyl-1-carboxylic acid, can be prepared according to the process described by T. Nakayama et al., Chem. Pharm. Bull., 32, 3968 (1984).

The products of general formula (I) can be purified according to the usual methods, such as chromatography.

The following examples illustrate the preparation of the products according to the invention.

EXAMPLE 1

5-Nitro-1,2,3,4-tetrahydronaphthyl-1(R,S)-carboxylic acid is prepared according to the method of Nakayama, T. et al., Chem. Pharm. Bull., 32, 3968 (1984).

1.24 g of (L)-methionine methyl ester hydrochloride, 0.84 g of 1-hydroxybenzotriazole, 0.9 cm³ of triethylamine and 1.28 g of dicyclohexylcarbodiimide are added to a solution of 1.23 g of 5-nitro-1,2,3,4tetraliydronaphthalene-1(R,S)-carboxylic acid in 25 cm³ of chloroform and 7.5 cm³ of dimethylformamide. The reaction mixture is stirred for 2 days at a temperature in the region of 20° C., filtered on sintered glass and then washed with 50 cm³ of chloroform. The organic solution is washed twice with 50 cm³ of a 10% (w/v) aqueous sodium hydrogencarbonate solution, then once with 50 cm³ of a 10% aqueous citric acid solution, once with distilled water and finally with a saturated aqueous sodium chloride solution. The organic phase is dried over magnesium sulphate, filtered and then concentrated to dryness under reduced pressure. 3.68 g of the methyl ester of N-(5-nitro-1,2,3,4-tetrahydronaphthyl-1(R,S)-carbonyl)-(L)-methionine are obtained in the form of an oil, the characteristics of which are the following:

proton nuclear magnetic resonance spectrum (300 MHz; d6-(CD$_3$)$_2$SO; δ in ppm; coupling constants J in Hz): 1.55–2.10 (mt, 6H, CH$_2$CH$_2$ at 2 and CH$_2$ at 3), 2.07 (s, 3H, SCH$_3$), 2.56 (mt, 1H, CH at 1), 4.45 (mt, 1H, CHCOO), 7.35–7.55 and 7.77 (2 mts, respectively 2H and 1H, H at 6 and H at 7 and H at 8), 8.63 and 8.69 (2d, J=8.5, 1H, CONH).

6.32 g of tin(II) chloride dihydrate are added to a solution of 3.68 g of the methyl ester of N-(5-nitro-1,2,3,4-tetrahydronaphthyl-1(R,S)-carbonyl)(L)-methionine in 100 cm³ of ethanol. The reaction mixture is stirred for 30 minutes at a temperature in the region of 70° C. and then cooled to a temperature in the region of 20° C. After dilution with 100 cm³ of ethyl acetate, the reaction mixture is poured onto ice and then brought to pH=7–8 by addition of a 5% aqueous sodium hydrogencarbonate solution. The mixture obtained is filtered on sintered glass covered with Celite. The organic phase is separated by settling and the aqueous phase is extracted twice with 150 cm³ of ethyl acetate. The organic phases are combined, dried over magnesium sulphate, filtered and concentrated to dryness under reduced pressure. 2.49 g of the methyl ester of N-(5-amino-1,2,3,4-tetrahydronaphthyl-1(R,S)-carbonyl)-(L)-methionine are thus obtained in the form of an oil, the characteristics of which are the following:

proton nuclear magnetic resonance spectrum (300 MHz, d6-(CD$_3$)$_2$SO; δ in ppm; coupling constants J in Hz): 1.50–2.10 (mt, 6H, CH$_2$CH$_2$ at 2 and CH$_3$ at 2), 2.10 (s, 3H, SCH$_3$), 2.39 and 2.53 (2 mts, each 2H, CH$_2$S and CH$_2$ at 4), 3.66 (mt, 1H, CH at 1), 3.69 (s, 3H, CHCOO), 4.75 (broad s, 2H, NH$_2$), 6.30–6.60 and 6.82 (2 mts, respectively 2H and 1H, H at 6 and H at 7 and H at 8), 8.48 (d, J=9, 1H, CONH).

3.73 g of S-triphenylmethyl-N-(tertbutoxycarbonyl) cysteinal, 0.48 cm³ of concentrated acetic acid, molecular sieve (3 A) and then 0.52 g of sodium cyanoborohydride are added to a solution of 1.24 g of the methyl ester of N-(5-amino-1,2,3,4-tetrahydronaphthyl-1(R,S)-carbonyl)-(L)-methionine in 60 cm³ of methanol. The reaction mixture is stirred for 2 days at a temperature in the region of 20° C. and then filtered on sintered glass, covered with Celite. The sintered glass is washed with methanol. The filtrate is concentrated to dryness under reduced pressure. The residue is dissolved in 150 cm³ of ethyl acetate and washed with 100 cm³ of a 10% (w/v) aqueous sodium hydrogencarbonate solution, 100 cm³ of a 10% (w/v) aqueous citric acid solution, 100 cm³ of distilled water, a further 100 cm³ of a 10% (w/v) aqueous sodium hydrogencarbonate solution and finally with 100 cm³ of a saturated aqueous sodium chloride solution. The organic phase is dried over magnesium sulphate, filtered and concentrated to dryness under reduced pressure. 5.62 g of the methyl ester of N-[5-(2(R)-tertbutoxycarbonylamino-3-(triphenylmethylmercapto)-propylamino)-1,2,3,4-tetrahydronaphthyl-1(R,S)carbonyl]-(L)-methionine are obtained in the form of a beige foam, the characteristics of which are the following:

proton nuclear magnetic resonance spectrum (300 MHz, d6-(CD$_3$)$_2$SO with a few drops of d4-CD$_3$COOD; δ in ppm; T=393K; coupling constants J in Hz): 1.38 (s, 9H, C(CH$_3$)$_3$), 1.50–2.05 (mt, 6H, CH$_2$CH$_2$ at 2 and CH$_2$ at 3), 2.06 (s, 3H, SCH$_3$), 2.05–2.45 and 2.53 (2 mts, respectively 4H and 2H, 2 CH$_2$S and CH$_2$ at 4), 2.85–3.05 (mt, 2H, NH2), 3.63 (mt, 1H, CH at 1), 3.63 and 3.67 (2 s, 3H, COOCH$_3$), 3.71 (mt, 1H, CHN), 4.43 (mt, 1H, CHCOO), 6.30–6.56 and 6.90 (2 mts, respectively 2H and 1H, H at 6 and H at 7 and H at 8), 7.15–7.35 (mt, 1SH, aromatic protons), 8.36 and 8.39 (2 poorly resolved d, J=10, 1H, CONH).

110 cm³ of trifluoroacetic acid are added, at a temperature in the region of 20° C., to a mixture of 5.45 g of the methyl ester of N-[5-(2(R)-tert-butoxycarbonylamino-3-(triphenylmethyl-mercapto)propylamino)-1,2,3,4-tetrahydronaphthyl-1 (R,S)-carbonyl]-(L)-methionine in 10 cm³ of ethanedithiol. The reaction mixture is stirred for 2 hours at a temperature in the region of 20° C. and is then concentrated under reduced pressure. The residue is triturated 3 times with 25 cm³ of ethyl ether and then dried under reduced pressure. The residue is purified by high performance liquid chromatography (C$_{18}$ phase), elution being carried out with an acetonitrile/water mixture containing 0.1% of trifluoroacetic acid. 0.4 g of the trifluoroacetate of the methyl ester of N-[5-(2(R)-amino-3-mercaptopropylamino)-1,2,3,4-tetrahydronaphthyl-1(R,S)-carbonyl]-(L)-methionine is obtained in the form of a powder, the characteristics of which are the following:

proton nuclear magnetic resonance spectrum (300 MHz; d6-(CD$_3$)$_2$SO with a few drops of d4-CD$_3$COOD; T=393° K; δ in ppm; coupling constants J in Hz):

1.55–2.10 (mt, 6H, $CH_2CH_2$ at 2 and $CH_2$ at 3), 2.04 (s, 3H, $SCH_3$), 2.30–2.65 and 2.80 (2 mts, respectively 4H and 2H, 2 $CH_2S$ and $CH_2$ at 4), 3.30 and 3.35–3.50 (respectively dd, J=14 and 8 and mt, each 1H, $NCH_2$), 3.43 (mt, 1H, CHN), 3.63 (mt, 1H, CH at 1), 3.63 (s, 3H, $COOCH_3$), 4.42 (Mt, 1H, CHCOO), 6.40–6.60 and 6.95 (2 mts, respectively 2H and 1H, H at 6 and H at 7 and H at 8), 8.35 and 8.38 (2 poorly resolved d, J=8, 1H, CONH).

elemental analysis: $C_{20}H_{31}N_3O_3S_2 \cdot 1.25SCF_3CO_2H$
Calculated %: C=47.7, H=5.70, N=7.4, S=11.9
Found: 47.8, 5.37, 7.1, 10.6

EXAMPLE 2

0.17 g of lithium hydroxide monohydrate ($LiOH.H_2O$) is added to a solution of 1.98 g of the methyl ester of N-[5-(2(R)-tert-butoxycarbonylamino-3-(triphenylmethylmercapto)propylamino)-1,2,3,4-tetrahydronaphthyl-1(R,S)-carbonyl](L)-methionine in 8.4 $cm^3$ of distilled water and 30 $cm^3$ of tetrahydrofuran. The solution is stirred for 20 hours at a temperature in the region of 20° C. and is then concentrated under reduced pressure. The residue is dissolved in distilled water. The pH is brought to 3 by addition of a 10% (w/v) aqueous citric acid solution. The aqueous phase is extracted 3 times with 100 $cm^3$ of ethyl acetate. The organic phases are combined, washed with a saturated aqueous sodium chloride solution, dried over magnesium sulphate, filtered and concentrated to dryness under reduced pressure. 1.92 g of N-[5-(2(R)-tert-butoxycarbonylamino- 3-(triphenylmethyl-mercapto) propylamino)-1,2,3,4-tetrahydronaphthyl-1(R,S)-carbonyl]-(L)-methionine are obtained in the form of a foam.

8 $cm^3$ of trifluoroacetic acid are added, at a temperature in the region of 20° C., to a mixture of 0.5 g of N-[5-(2(R)-tert-butoxycarbonylamino-3-(triphenyl-methylmercapto) propylamino)-1,2,3,4-tetrahydronaphthyl-1(R,S)-carbonyl]-(L)-methionine in 2.5 $cm^3$ of triethylsilane. The reaction mixture is stirred for 2 hours at a temperature in the region of 20° C. and is then concentrated under reduced pressure. The residue is triturated 3 times with 25 $cm^3$ of ethyl ether and then dried under reduced pressure. The residue is purified by high performance liquid chromatography ($C_{18}$ phase), elution being carried out with an acetonitrile/water mixture containing 0.1% of trifluoroacetic acid. 0.094 g of the trifluoroacetate of N-[5-(2(R)-amino-3-mercaptopropylamino)-1,2,3,4-tetrahydronaphthyl-1(R,S)-carbonyl]-(L)-methionine is obtained in the form of a powder, the characteristics of which are the following:

proton nuclear magnetic resonance spectrum (300 MHz, d6-$(CD_3)_2SO$; δ in ppm; coupling constants J in Hz): 1.55–2.10 (mt, 6H, $CH_2CH_2$ at 2 and $CH_2$ at 3), 2.06 (s, 3H, $SCH_3$), 2.30–2.65 and 2.75–2.30 (2 mts, respectively 4H and 2H, 2 $CH_2S$ and $CH_2$ at 4), 3.30 and 3.35–3.50 (respectively dd, J=14 and 8 and mt, each 1H, $NCH_2$), 3.43 (mt, 1H, CHN), 3.66 (mt, 1H, CH at 1), 4.37 (mt, 1H, CHCOO), 6.40–6.60 and 6.95 (2 mts, respectively 2H and 1H, H at 6 and H at 7 and H at 8), 7.95 (broad s, 3H, $NH_3^+$), 8.33 and 8.35 (2 d, J=9, 1H, CONH).

elemental analysis: $C_{19}H_{29}N_3O_3S_2 \cdot 1.33CF_3CO_2H$
Calculated %: C=46.2, H=5.42, N=7.46, S=11.38 F=13.46
Found: 45.8, 5.5, 7.47, 11.25 13.2

The inhibitory activity with respect to farnesyl transferase and to farnesylation of the Ras. protein may be demonstrated in the following test:

Farnesyl transferase activity is determined by the quantity of [$^3H$]farnesyl transferred from [$^3H$]farnesyl pyrophosphate ([$^3H$]FPP) to the p21 H-Ras protein. The standard reaction mixture is composed, for a final volume of 60 μl, of 50 mM Tris-HCl, 5 mM $MgCl_2$, 5 mM dithiotreitol, 0.2% octyl β-D-glucopyranoside, 200 picomol p21 H-ras, 4.5 picomol [$^3H$]FPP (activity 61000 dpm/picomol).

Reaction is initiated by adding approximately 5 ng of human farnesyl transferase purified from THP1 cell cultures. After incubation for 20 minutes at 37° C. in a microtitration plate containing 96 1-$cm^3$ wells per plate (Titer Plate®, Beckman), the reaction is stopped by adding 0.4 $cm^3$ of 0.1% SDS in methanol at 0° C. The mixture is then treated with 0.4 $cm^3$ of 30% trichloroacetic acid (TCA) in methanol. The plates are left in ice for 1 hour. The precipitated contents are then retained on Filtermat®, Pharmacia) glass fibre membranes with the filtration unit (Combi Cell Harvester®, Skatron), and rinsed with 6% trichloroacetic acid in distilled water. The membranes are dried in a microwave oven, then impregnated with scintillation medium by melting of Meltilex® (Pharmacia) under hot air, and lastly counted in cpm in a β-Plate counter® (LKB). Each test is repeated 3 times.

The unit of activity is defined as 1 picomole of [$^3H$]FPP transferred to p21 H-Ras in 20 minutes.

The percentage inhibition values are obtained by comparison of the tests with and without inhibitor after deduction of blanks, the $IC_{50}$ values being measured on the basis of the inhibitions obtained with 9 different concentrations using Enzfitter® or Grafit® software.

The activity against cells can be determined in the following way:

The cell line is the THAC line (CCL 39 cells transfected with activated Ha-Ras) according to K. Seuwen et al., EMBO J., 7(1) 161–168 (1988). The cells are cultured in Petri dishes with a diameter of 6 cm containing a DMEM medium, 5% foetal calf serum and 1% G418.

After culturing for 24 hours, the culture medium is changed (with or without the serum).and the product to be studied is added in solution in dimethylformamide (DMF), in the presence or in the absence of DTT (final concentrations of 0.5% in DMF and 0.1 mM in DTT). After culturing for 24 hours at 37° C., the cells are lysed in 1 $cm^3$ of lysis buffer (20 mM Tris, HCl, 1% Triton X114, 5 mM $MgCl_2$, 7 mM DTT, 150 mM NaCl, pH=7.4). The lysates are clarified by centrifuging at 4000 revolutions/minute for 10 minutes. Extraction with Triton X114 makes it possible to separate the farnesylated Ras protein from the non-farnesylated Ras protein (C. Bordier, J. Biol. Chem., 256 (4), 1604–1607 (1981)]. The farnesylated Ras protein, which is more hydrophobic, is found in the detergent phase whereas the non-farnesylated Ras protein is in the aqueous phase. The samples are denatured by heating at 95° C. in the denaturation buffer for electrophoresis and deposited on a 14% polyacrylamide gel. When the dye reaches the bottom of the gel, the proteins of the gel are transferred onto a PVDF membrane. The Ras protein is visualized by the Western blot technique: the membrane is incubated with an anti-Ras specific monoclonal antibody (pan-Ras Ab3, Oncogène Science) and then with protein A labelled with $^{125}I$. After autoradiography, the bands are identified, cut out and counted in a γ counter. The radioactivity of the bands corresponding to farnesylated Ras and to non-farnesylated Ras makes it possible to determine the percentage of inhibition of farnesylation of the Ras protein.

The results obtained are collated in Table I.

TABLE I

| PRODUCT | Inhibitory activity IC$_{50}$ nM | % of inhibition against cells (THAC) |
|---|---|---|
| Example 1 | 15 | >10 (10 µM) |
| Example 2 | 405 | 50 (50 µM) |

The new products of general formula (I) can be in the form of non-toxic and pharmaceutically acceptable salts. These non-toxic salts comprise the salts with inorganic acids (hydrochloric, sulphuric, hydrobromic, phosphoric and nitric acids) or with organic acids (acetic, propionic, succinic, maleic, hydroxymaleic, benzoic, fumaric, methanesulphonic, trifluoroacetic or oxalic acid), or with inorganic bases (sodium hydroxide, potassium hydroxide, lithium hydroxide, calcium hydroxide) or organic bases (tertiary amines such as triethylamine, piperidine, benzylamine), depending on the nature of the $R_1$ and R symbols of the product of general formula (I).

The present invention also relates to pharmaceutical compositions containing at least one product of general formula (I), in combination with one or more pharmaceutically acceptable diluents or adjuvants, which may be either inert or physiologically active.

These compositions may be administered orally, parenterally or rectally.

The compositions for oral administration comprise tablets, pills, powders or granules. In these compositions, the active product according to the invention is mixed with one or more inert diluents such as sucrose, lactose or starch. These compositions can comprise substances other than diluents, for example lubricants such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, for example wetting, sweetening or flavouring products.

The compositions according to the invention for parenteral administration can be sterile solutions, aqueous or non-aqueous, suspensions or emulsions. As solvent or vehicle, propylene glycol, a polyethylene glycol, vegetable oils, especially olive oil, or injectable organic esters, for example ethyl oleate, may be employed. These compositions can also contain adjuvants, especially wetting, emulsifying and dispersing agents. The sterilization may be carried out in several ways, for example using a bacteriological filter, by incorporating sterilizing agents in the composition or by heating. They may also be prepared in the form of sterile solid compositions which can be dissolved at the time of use in sterile water or any other sterile injectable medium.

The compositions for rectal administration, are suppositories which can contain, besides the active product, excipients such as cocoa butter.

The compositions according to the invention are especially useful in human therapy in the treatment of cancers of various origins.

In human therapy, the doses depend on the effect sought, the period of treatment and factors specific to the subject to be treated.

Generally, in man, the doses are between 0.1 and 20 mg/kg per day via the intraperitoneal route.

A composition according to the invention is illustrated in the following example.

EXAMPLE 200 mg of the product obtained in Example 1 are dissolved in 100 cm$^3$ of physiological serum. The solution obtained is divided up aseptically into 10 cm$^3$ phials.

The phials are administered as a single injection or by perfusion.

We claim:

1. A compound therefor of general formula:

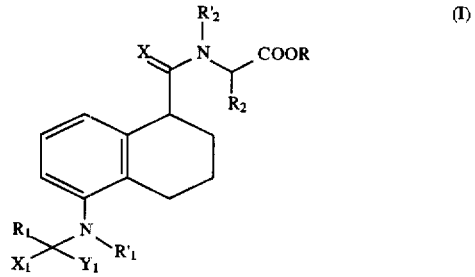

in which:

$R_1$ represents a radical of general formula Y—S—A$_1$— in which Y represents a hydrogen atom or an amino acid residue or a fatty acid residue or an alkyl or alkoxycarbonyl radical, and A$_1$ represents a straight or branched alkylene radical containing 1 to 4 carbon atoms, optionally substituted at the position α to the >C(X$_1$) (Y$_1$) group by an amino, alkylamino, alkanoylamino or alkoxycarbonylamino radical, the straight or branched alkyl or alkanoyl part of which contains 1 to 6 carbon atoms.

X$_1$ and Y$_1$ each represent a hydrogen atom or form, together with the carbon atom to which they are bonded, a >C=O group, R'$_1$ represents a hydrogen atom or a straight or branched alkyl radical containing 1 to 6 carbon atoms, X represents an oxygen or sulphur atom, R$_2$ represents a straight or branched alkyl, alkenyl or alkynyl radical containing 1 to 6 carbon atoms, optionally substituted by a hydroxyl radical, an alkoxy radical containing 1 to 4 carbon atoms, a mercapto radical, an alkylthio radical containing 1 to 4 carbon atoms, an alkylsulphinyl radical containing 1 to 4 carbon atoms or an alkylsulphonyl radical containing 1 to 4 carbon atoms, it being understood that, when R$_2$ represents an alkyl radical substituted by a hydroxyl radical, R$_2$ can form a lactone with the carboxyl radical at the α position, R'$_2$ represents a hydrogen atom or a straight or branched alkyl radical containing 1 to 6 carbon atoms, and R represents a hydrogen atom or an alkyl radical containing 1 to 6 carbon atoms, optionally substituted by an alkoxy radical containing 1 to 4 carbon atoms, an alkylthio radical containing 1 to 4 carbon atoms, an alkylsulphinyl radical containing 1 to 4 carbon atoms, an alkylsulphonyl radical containing 1 to 4 carbon atoms, a phenyl radical, a phenoxy radical, a phenylthio radical, a phenylsulphinyl radical, a phenylsulphonyl radical, an alkylamino radical containing 1 to 4 carbon atoms or a dialkylamino radical in which each alkyl part contains 1 to 4 carbon atoms, or a phenyl radical, optionally substituted by one or a number of atoms or radicals chosen from halogen atoms and alkyl, alkyloxy, alkylthio or alkanoyl radicals.

2. A compound therefor according to claim 1 in which:

$R_1$ represents a radical of formula Y—S—A$_1$— in which Y represents a hydrogen atom or a lysine residue or a fatty acid residue containing up to 20 carbon atoms and $A_1$ represents an ethylene or propylene radical optionally substituted by an amino radical, $X_1$ and $Y_1$ each represent a hydrogen atom or form, together with the carbon atom to which they are bonded, a >C=O group.

$R'_1$ represents a hydrogen atom or a methyl radical,

X represents an oxygen atom, $R_2$ represents an alkyl radical containing 1 to 4 carbon atoms, optionally substituted by a hydroxyl, methoxy, mercapto, methylthio, methylsulphinyl or methylsulphonyl radical, $R'_2$ represents a hydrogen atom or a methyl radical, and R represents a hydrogen atom or an alkyl radical containing 1 to 4 carbon atoms, optionally substituted by an alkoxy radical, or a phenyl radical.

3. A compound therefor according to claim 1 in which:

$R_1$ represents a radical of formula $Y$—$S$—$A_1$— in which Y represents a hydrogen atom and $A_1$ represents an ethylene or propylene radical optionally substituted by an amino radical, $X_1$ and $Y_1$ each represent a hydrogen atom or form, together with the carbon atom to which they are bonded, a >C=O group, $R'_1$ represents a hydrogen atom, X represents an oxygen atom, $R_2$ represents a methyl, ethyl, propyl or butyl radical optionally substituted by a hydroxyl, methoxy, mercapto or methylthio radical, $R'_2$ represents a hydrogen atom, and R represents a hydrogen atom or an alkyl radical containing 1 to 4 carbon atoms.

4. A compound therefor according to claim 1 in which $R_1$ represents a 2-mercaptoethyl or 1-amino-2-mercaptoethyl radical, $X_1$ and $Y_1$ each represent a hydrogen atom or form, together with the carbon atom to which they are bonded, a >C=O group, $R'_1$ represents a hydrogen atom, X represents an oxygen atom, $R_2$ represents an n-butyl or 2-(methylthio) ethyl radical and $R'_2$ represents a hydrogen atom, and R represents a hydrogen atom or a methyl radical.

5. Pharmaceutical composition, characterized in that it contains a sufficient amount of the compound according to claim 1 in combination with one or a number of inert or physiologically active pharmaceutically acceptable diluents or adjuvants.

* * * * *

UNITED STATES PATENT AND TRADEMARK OFFICE
CERTIFICATE OF CORRECTION

PATENT NO.    : 5,750,567
DATED         : May 12, 1998
INVENTOR(S)   : Bernard Baudoin, et. al.

It is certified that error appears in the above-identified patent and that said Letters Patent is hereby corrected as shown below:

Title page, item [57],

On the last line of the patent's abstract, after "alkylsulphonyl", please insert --, with the proviso that when $R_2$ is an alkyl radical substituted by a hydroxy radical, then $R_2$ and the $\alpha$ carboxy radical can form a lactone; $R'_2$ is hydrogen or a $C_{1-6}$ alkyl radical; and R is a hydrogen atom, an optionally substituted alkyl radical or an optionally substituted phenyl radical. Said novel products have anticancer properties--.

At column 1, line 46, please delete "a" and insert --$\alpha$-- therefor.

At column 2, line 25, after "bonded," please insert --a >C=O group,-- therefor;
line 26, please delete "a >C=O group,";
line 46, after "bonded," please insert --a >C=O group,--;
line 47, please delete "a >C=O group,".

At column 4, line 38, please delete "as." and insert --as-- therefor;
line 61, please delete "a" and insert --$\alpha$-- therefor.

At column 5, line 32-33, please delete "5-nitro-1,2,3,4tetrahydronaphthalene-1(R,S)-carboxylic acid" and insert --5-nitro-1,2,3,4-tetrahydronaphthalene-1(R,S)-carboxylic acid-- therefor;

UNITED STATES PATENT AND TRADEMARK OFFICE
CERTIFICATE OF CORRECTION

PATENT NO.    : 5,750,567
DATED         : May 12, 1998
INVENTOR(S)   : Bernard Baudoin, et. al.

It is certified that error appears in the above-identified patent and that said Letters Patent is hereby corrected as shown below:

At column 7, line 10, please delete "$C_{20}H_{31}N_{30}O_3S_2 \cdot 1.25SCF_3CO_2H$ and insert --$C_{20}H_{31}N_{30}O_3S_2 \cdot 1.25CF_3CO_2H$-- therefor;

--$C_{20}H_{31}N_3O_3S_2 \cdot 1.25CF_3CO_2H$-----

At column 8, line 10, please delete "Plate®" and insert --Plate®-- therefor;
line 15, please delete "Filtermat®" and insert --Filtermat®-- therefor;
line 16, please delete "Harvester®" and insert --Harvester®-- therefor;
lines 19-20, please delete "Meltilex®" and insert --Meltilex®-- therefor;
line 21, please delete "counter®" and insert --counter®-- therefor;
line 30, please delete "Enzfitter®" and insert --Enzfitter®-- therefor;
line 30, please delete "Grafit®" and insert --Grafit®-- therefor;

At column 10, line 8, please delete "therefor";
line 64, after "radicals" please insert --, or a pharmaceutically acceptable salt thereof--;
line 65, please delete "therefor".

UNITED STATES PATENT AND TRADEMARK OFFICE
CERTIFICATE OF CORRECTION

PATENT NO.    :    5,750,567
DATED         :    May 12, 1998
INVENTOR(S)   :    Bernard Baudoin, et. al.

It is certified that error appears in the above-identified patent and that said Letters Patent is hereby corrected as shown below:

At column 11, line 5, after "bonded," please insert --a >C=O group,--;
line 6, please delete "a >C=O group,";
line 17, after "phenyl radical" please insert --, or a pharmaceutically acceptable salt thereof--;
line 18, please delete "therefor";
line 25, after "bonded," please insert --a >C=O group,--.

At column 12, line1, please delete "a >C=O group,";
line 10, after "atoms" please insert --, or a pharmaceutically acceptable salt thereof--.
line 11, please delete "therefor".
line 18, after "radical" please insert --, or a pharmaceutically acceptable salt thereof--.

UNITED STATES PATENT AND TRADEMARK OFFICE
CERTIFICATE OF CORRECTION

PATENT NO.    :    5,750,567
DATED         :    May 12, 1998
INVENTOR(S)   :    Bernard Baudoin, et. al.

It is certified that error appears in the above-identified patent and that said Letters Patent is hereby corrected as shown below:

At column 12, lines 19-23, please delete
"5.    Pharmaceutical composition, characterized in that it contains a sufficient amount of a product according to one of claims 1 to 4 in combination with one or a number of inert or physiologically active pharmaceutically acceptable diluents or adjuvants."
and insert
-- 5.    A pharmaceutical composition comprising a pharmaceutically effective amount of a compound according to claim 1, or a salt thereof, and an inert or physiologically active pharmaceutically acceptable diluent or adjuvent.

6.    A compound according to claim 1 selected from:
   N-[5-(2(R)-amino-3-mercapto-propylamino)-1,2,3,4-tetrahydronaphthyl-1(R,S)-carbonyl]-(L)-methionine;
   N-[5-(2(R)-amino-3-mercapto-propylamino)-1,2,3,4-tetrahydronaphthyl-1(R,S)-carbonyl]-(L)-methionine methyl ester; or
   a trifluoroacetate salt thereof.-- thereof.

Signed and Sealed this

Twenty-second Day of December, 1998

Attest:

BRUCE LEHMAN

*Attesting Officer*          *Commissioner of Patents and Trademarks*